(12) United States Patent
Rice et al.

(10) Patent No.: US 7,388,971 B2
(45) Date of Patent: Jun. 17, 2008

(54) ROBUST AND LOW COST OPTICAL SYSTEM FOR SENSING STRESS, EMOTION AND DECEPTION IN HUMAN SUBJECTS

(75) Inventors: Robert R. Rice, Simi Valley, CA (US); Barry Dunbridge, Torrance, CA (US)

(73) Assignee: Northrop Grumman Corporation, Los Angeles, CA (US)

( * ) Notice: Subject to any disclaimer, the term of this patent is extended or adjusted under 35 U.S.C. 154(b) by 624 days.

(21) Appl. No.: 10/692,999

(22) Filed: Oct. 23, 2003

(65) Prior Publication Data
US 2005/0089206 A1    Apr. 28, 2005

(51) Int. Cl.
*G06K 9/00* (2006.01)
*G06K 9/36* (2006.01)

(52) U.S. Cl. .................................... 382/118; 382/236
(58) Field of Classification Search ............... 382/118, 382/218, 236, 190, 209, 294; 348/143, 402; 396/129
See application file for complete search history.

(56) References Cited

U.S. PATENT DOCUMENTS

| | | | |
|---|---|---|---|
| 4,818,101 A | 4/1989 | Soreide et al. | |
| 5,268,729 A * | 12/1993 | Kunishige | 396/129 |
| 5,507,291 A * | 4/1996 | Stirbl et al. | 600/407 |
| 5,710,833 A | 1/1998 | Moghaddam et al. | |
| 5,774,591 A * | 6/1998 | Black et al. | 382/236 |
| RE36,041 E | 1/1999 | Turk et al. | |
| 5,867,257 A | 2/1999 | Rice | |
| 6,388,739 B1 | 5/2002 | Rice | |
| 6,526,161 B1 | 2/2003 | Yan | |
| 6,549,644 B1 * | 4/2003 | Yamamoto | 382/118 |
| 6,598,478 B2 | 7/2003 | Rice | |
| 6,600,830 B1 | 7/2003 | Liu et al. | |
| 6,600,946 B1 | 7/2003 | Rice | |
| 6,611,613 B1 | 8/2003 | Kang et al. | |
| 6,785,410 B2 * | 8/2004 | Vining et al. | 382/128 |
| 6,810,135 B1 * | 10/2004 | Berenz et al. | 382/118 |
| 6,879,709 B2 * | 4/2005 | Tian et al. | 382/118 |

(Continued)

OTHER PUBLICATIONS

Pantic et al; "Expert system for automatic analysis of facial expression"; Jan. 25, 2000; Image and Vision Computing; 18 (2000) 881-905.*

(Continued)

*Primary Examiner*—Andrew W. Johns
*Assistant Examiner*—Andrae Allison
(74) *Attorney, Agent, or Firm*—Tarolli, Sundheim, Covell & Tummino LLP

(57) ABSTRACT

A method and related apparatus for sensing selected emotions or physical conditions in a human subject. The technique employs a two-dimensional camera to generate a facial image of a human subject. Then, an image processing module scans the image to locate the face position and extent, and then scans for selected critical areas of the face. The size and activity of the selected critical areas are monitored by comparing sequential image frames of the subject's face, and the areas are tracked to compensate for possible movements of the subject. The sensed parameters of the selected critical areas are compared with those stored in a database that associates activities of the critical areas with various emotional and physical conditions of the subject, and a report or assessment of the subject is generated.

15 Claims, 3 Drawing Sheets

U.S. PATENT DOCUMENTS

| | | | |
|---|---|---|---|
| 6,959,102 B2* | 10/2005 | Peck | 382/103 |
| 7,003,139 B2* | 2/2006 | Endrikhovski et al. | 382/118 |
| 7,095,901 B2* | 8/2006 | Lee et al. | 382/255 |

OTHER PUBLICATIONS

Black et al; "Recognizing Facial Expression in Image Sequence Using Local Parameterized Models of Image Motion", Aug. 9, 1996; International Journal of Computer Vision ; 23-48 (1997).*

Yaser et al; "Recognizing Human Facial Expressions From Long Image Sequences Using Optical Flow"; Jun. 1996; IEEE Transaction on Pattern Analysis and Machine Intelligence; vol. 18, No. 6.*

Reilly; "Applications of face and gesture recognition for human-computer interaction"; Proceedings of the sixth ACM international conference on Multimedia: Face/gesture recognition and their applications Bristol, United Kingdom; pp. 20-27; Year of Publication: 1998.*

J. Gryzagoridis, "Fundamentals of Holographic Interferometry, Electronic Speckle Pattern Interferometry (ESPI) and Shearography," Mechanical Engeineering Department University of Cape Town, Cape Town, RSA.

ESPI Technology, "ESPI Measurement (electronic speckle pattern interferometry) Background, theory and practice," http://www.syncretek.com/espi technology.htm.

Essa I A et al: "Coding, Analysis, Interpretation, and Recognition of Facial Expressions", IEEE Transactions on Pattern Analysis And Machine Intelligence, IEEE Inc., New York vol. 19, No. 7, Jul. 1997.

Tian Y-L et al: "Recognizing Action Units for Facial Expression Analysis", IEEE Transactions on Pattern Analysis ANd Machine Intelligence, IEEE Inc., New York vol. 23, No. 2, 1, Feb. 2001.

* cited by examiner

ROBUST AND LOW COST OPTICAL SYSTEM FOR SENSING STRESS, EMOTION AND DECEPTION IN HUMAN SUBJECTS

BACKGROUND OF THE INVENTION

The present invention relates generally to biometric techniques for sensing stress and emotion in human subjects and, more particularly, to non-invasive, optical systems and methods for sensing stress and emotion. The underlying principle on which the present invention is based is that internal emotional and physiological states of a human subject are correlated with transient and vibratory surface motions of the skin, and that these motions provide insight into the subject's physiological and psychological state. Moreover, this insight can enable a reliable assessment of the affect and credibility of the subject through the application of algorithms based on established databases.

More specifically, the relationships between emotions and a subject's facial expressions and movements have been well documented by Paul Ekman and others. The Facial Action Coding System (FACS), by Paul Ekman, Wallace V. Friesen and Joseph C. Hager, originally published in 1978 by Paul Ekman, University of California at San Francisco, San Francisco, Calif., includes an ACS Manual and other materials defining the emotion-expression relationships in detail. Dr. Ekman has authored or edited numerous other published papers and books in the same subject matter. See, for example, "What The Face Reveals: Basic and Applied Studies of Spontaneous Expression Using The Facial Action Coding System (FACS)," Ekman, P. & Rosenberg, E. L. (editors), Oxford University Press, New York, 1997.

The best known prior art technique for making such measurements of facial features and movements was based on the use of laser Doppler vibrometry (LDV) and relatively primitive electro-mechanical sensors. LDV is a technique for detecting surface vibration without physical contact and is widely used in engineering and manufacturing applications.

As useful as LDV has proven to be for making measurements of facial movements, the method has significant drawbacks. A laser beam must be pointed at a specific test point on the subject's skin that is believed to be indicative of an emotional state. The vibrations or transient motions induce frequency modulation on light that is reflected back to the instrument, and well-known heterodyne laser detection methods are used to recover the mechanical signal for display and processing. The beam must be maintained on the test point to make the measurement, and this requirement presents some practical problems, in general requiring that the subject's movements be constrained to some degree during the test.

A more serious limitation is that only a single point can be examined at a time with conventional LDV hardware. While it is known that monitoring many points on the subject's skin simultaneously provides significant information concerning the subject's affect, a separate LDV instrument would be required to monitor the response at each point to capture all of the spontaneous facial movements needed to detect a particular emotional condition. The pioneering work of Ekman and Friesen on micro-expressions showed that many facial muscle groups are involved in the involuntary transient expression of emotion. For a brief time of about 300 ms (milliseconds) or so, the face of a subject responds involuntarily to emotion-evoking stimuli such as questions, comments, or scenes, and these fleeting expressions can be detected and interpreted. The Facial Action Coding System developed by Ekman et al. maps specific emotions to coordinated motions in more that twenty facial muscle groups. Hence, being unable to monitor all or most of these muscle groups at the same time is a serious limitation for LDV instruments.

Lastly, signal processing for the received signal in an LDV instrument is somewhat problematic, requiring algorithms to remove subject motion artifacts. The LDV is useful for making high fidelity measurement of skin surface movements for cardiology and other applications, but it would be highly desirable if the motions of an entire face could be sensed at an instant, so that correlated responses among muscle groups could be detected and processed. The present invention is directed to this end.

SUMMARY OF THE INVENTION

The present invention resides in a method and apparatus for sensing emotional and physical conditions of a human subject by evaluating movements in selected areas of the subject's face. Briefly, and in general terms, the method of the invention comprises the steps of generating an image of substantially all of the face of a human subject; processing the image to identify movements in selected critical areas of the face; comparing the identified movements in the selected critical areas with a database that associates movements in selected critical areas with specific emotional and physical conditions; and generating a report of the emotional and physical condition of the subject.

More specifically, the processing step comprises inputting a two-dimensional frame of the image; scanning the image to locate the subject's face and determine it's relative position and extent; scanning the facial part of the image to detect the selected critical areas; repeating the preceding steps for a sequence of image frames; recording frame-to-frame changes in critical areas of interest; and recording frame-to-frame changes in critical area positions, for purposes of tracking the positions while permitting limited movement of the subject.

In apparatus terms, the invention comprises an optical imaging device, for generating an image of substantially all of the face of a human subject; an image processing module, for processing the image to identify movements in selected critical areas of the face; a database that associates groups of facial movements with specific emotional and physical conditions of the subject; a database analysis module, for comparing the identified movements in the selected critical areas with the database; and a report generator, for generating a report of the emotional and physical condition of the subject.

It will be appreciated from the foregoing brief summary that the present invention represents a significant advance in the field of human emotion sensing apparatus and methods. In particular, the present invention images substantially the entire facial image of the subject, and senses and tracks multiple critical areas of the image simultaneously, comparing the results with a database to obtain an assessment of the subject's emotional and physical condition. Other aspects and advantages of the invention will become apparent from the following more detailed description of the invention.

DETAILED DESCRIPTION OF THE INVENTION

Figure 1:
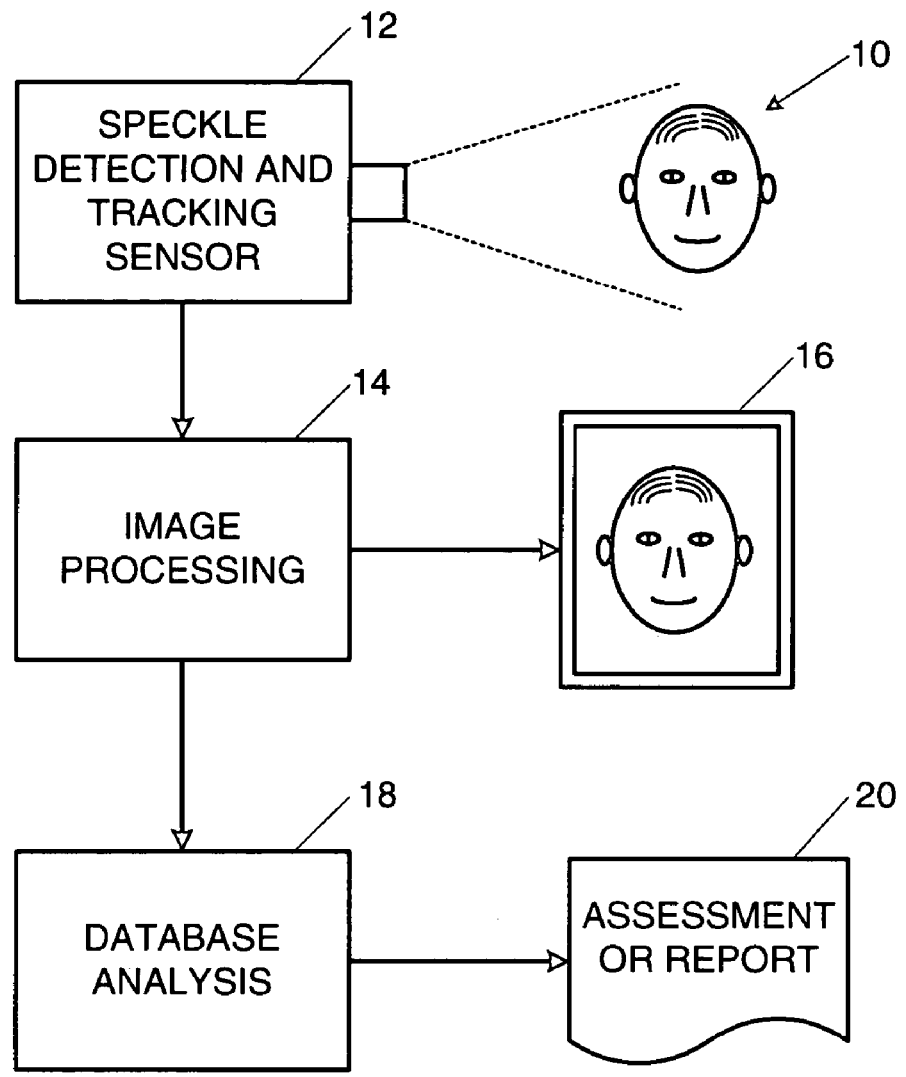
FIG. 1 is block diagram showing the principal components of the present invention.

As shown in the drawings for purposes of illustration, the present invention is concerned with an optical technique for detecting involuntary movements of the face of a human subject, and using the detected movements to report various emotional conditions, such as stress and deception, experienced by the subject. Prior to the present invention, detection of movement in a facial feature of interest has been accomplished using a laser beam and a technique known as laser Doppler vibrometry (LDV). The LDV approach has a number of significant disadvantages, which have been discussed above.

In accordance with the invention, a human subject's entire face is rapidly scanned to detect movements in critical areas that are known to be affected involuntarily when the subject is exposed to various emotion-provoking stimuli, and the detected responses are compared with a database that associates the responses with specific emotions or physiological conditions. As shown in FIG. 1, a subject, indicated diagrammatically by a face 10, is imaged by a speckle detection and tracking sensor 12. The term "speckle" is derived from "laser speckle," a sparkling granular pattern that is observed when an object diffusely reflects coincident laser light. The laser speckle pattern has been used to make surface measurements of objects, with techniques known as speckle metrology or speckle interferometry. In the present context, use of the term "speckle" is not intended to limit the invention to the use of lasers to illuminate the subject. On the contrary, the invention is intended to operate using available light or, as will be further discussed, a narrow-band source outside the visible spectrum.

The sensor 12 may be any two-dimensional full-frame digital camera device, using, for example, CCD (charge-coupled device) technology or CMOS (complementary metal-oxide semiconductor) imaging devices. If laser illumination is used, the sensor 12 may use electronic speckle pattern interferometry (ESPI), such as the ESPI sensors made by Steinbishler Optotechnik GmbH.

Figure 2:
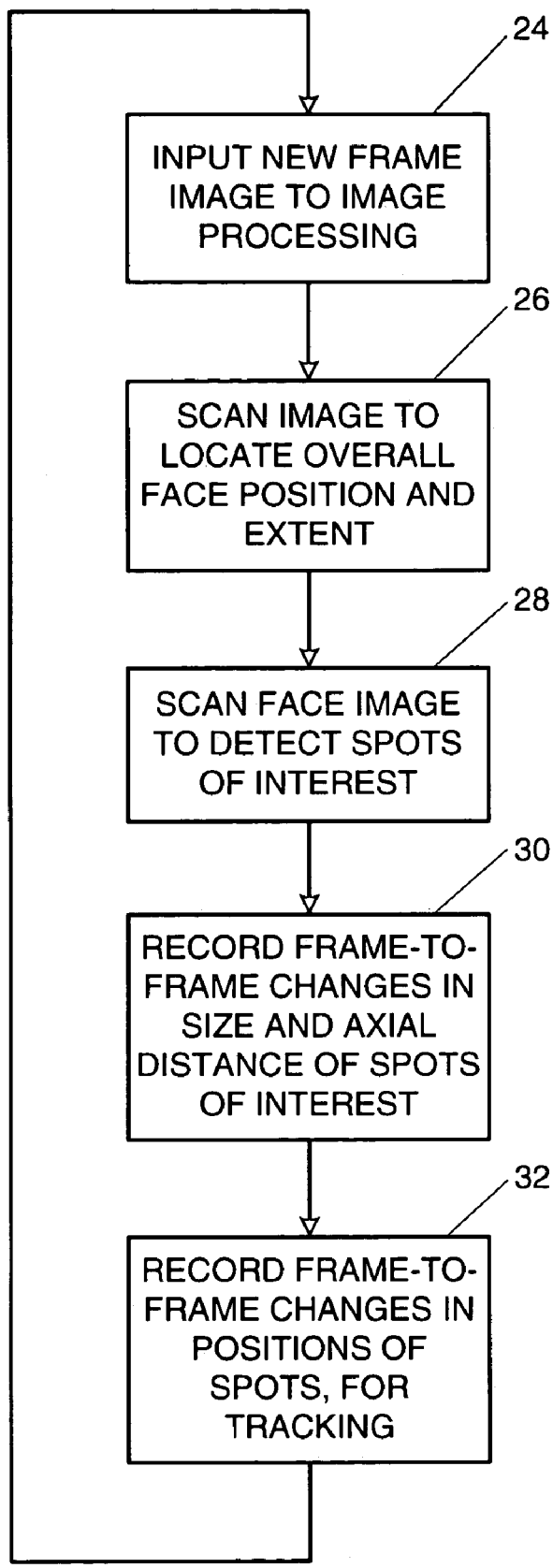
FIG. 2 is a flowchart depicting the principal functions performed by an image processing module in the present invention.

Image data produced by the sensor 12 are processed in an image processing module 14 to detect and track "speckle spots" on the subject's face, as described more fully with reference to FIG. 2. The processed image may be supplied to a display 16 for use by an operator of the apparatus. Data concerning the identified spots of interest on the subject's face are transferred to a database analysis module 18, which compares the identified spots with a database of known associations between facial movements and emotional and physiological conditions. From this comparison, the database analysis module 18 generates an assessment or report 20. The assessment may be merged with the display data fed to the display 16, to alert the operator to critical conditions or conclusions concerning the face of the subject 10.

Processing the captured image of the subject 10 can take various forms. The basic processing steps performed in the image processing module 14 are shown in FIG. 2. After a new frame of the image has been input to the processing module 14, as indicated by block 24, the next step is to scan the image to locate the face position and its extent in the image, as indicated in block 26. The face outline and position are located with reference to its known standard features, such as ears, eyes, nose, mouth and chin. Facial feature extraction is known in the art of biometrics, and various techniques for identifying and locating the principal facial features have been the subject of research and publication. For example, the following patents disclose such techniques: U.S. Pat. No. 6,600,830 B1, issued Jul. 29, 2003 to Chun-Hung Lin and Ja-Ling Wu, entitled "Method and System of Automatically Extracting Facial Features," and U.S. Pat. No. 6,526,161 B1, issued Feb. 25, 2003 to Yong Yan, entitled "System and Method for Biometrics-Based Facial Feature Extraction." To the extent that these two patents are deemed necessary to a complete disclosure of the present invention, they are hereby incorporated by reference into this description.

Once the face and its principal features have been located within the two-dimensional image, the next step is to detect and locate critical muscle spots that are known to be subject to vibration or transient movement when the subject is exposed to emotion-evoking stimuli. The positions of these critical muscle spots with respect to the principal facial features are known in advance, at least approximately, from the works of Ekman and others, and particularly from Ekman's Facial Action Coding System. The locations of the muscle spots or "speckle spots" can be more precisely determined using any of at least three algorithmic search methods.

One method for locating the critical spots is 2-D (two-dimensional) image motion sensing, i.e., the detection of repetitive fluctuation of reflected light in the speckle spot, corresponding to facial muscle vibrational movements. This algorithmic approach enables detection and location acquisition by means of a processing algorithm using the inputted 2-D imaging pixel data, which then looks for local multiple-pixel reflectivity fluctuations (frame to frame), compared to non-vibratory areas of the adjacent facial surfaces. The frame rate must be high enough to sense the peaks and valleys of speckle reflectivity changes.

Another approach is 3-D (three-dimensional) dimple motion sensing. Dimple motion is a repetitive fluctuation of speckle spots orthogonal to facial skin, equivalent to dimples that can sometimes be visually observed. Orthogonal, in this context, means in the same direction as the camera focal axis. Dimpling must be sensed as a change in distance from the camera or sensor 12. The dimpling movement of the speckle spot is driven by vibratory local facial muscles. This algorithmic approach can be achieved using range measurement 3-D, full frame camera methods. The range resolution must be compatible with expected changes in dimple/speckle movements, and should be no more than approximately 0.5 mm or slightly larger.

Another approach is to use double sampled (pulse frame differenced) imaging for 2-D or 3-D motion sensing. This method utilizes an actively illuminated, pulsed source at a near infrared (IR) wavelength, which provides cancellation of background illumination (sunlight, shadowing) by subtracting the 2-D image at the end of the pulse period, from the 2-D image at the beginning of the pulse period. The principal advantage of the method is a high contrast ratio in the resulting image, since slow variations in both high brightness (direct sunlight), and shadowed environments (outdoors or indoor) will be eliminated. This makes a subsequent motion sensing step much more accurate.

As indicated in block 30, image processing includes recording frame-to-frame changes in the size and axial distance of the spot of interest. As indicated above, such changes are used in various approaches to detect the presence and locations of the spots initially, as well as to detect changes in the spots in terms of their extent and axial distance, as measured over a selected time interval. As indicated in block 32, there is also a requirement to track frame-to-frame positions of spots in order to compensate for movement of the subject or the subject's face. In general, tracking and temporal recording of the speckle spots is effected by measuring the continuing temporal occurrence and magnitude intensity changes of the spots. This is the desired data that will be both stored and temporally marked to correlate to other events (e.g., questions from the examiner) to sense the emotional behavior and status of the individual being examined.

Figure 3:
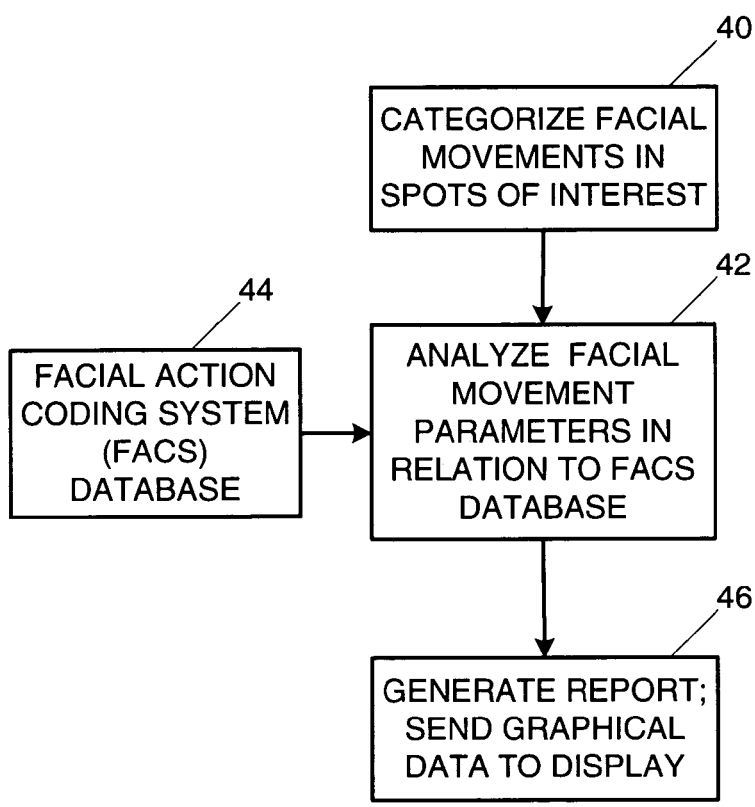
FIG. 3 is a flowchart depicting the principal functions performed by a database analysis module in the present invention.

The database analysis module 18 (FIG. 1) performs the steps outlined in FIG. 3. As indicated in block 40, the image data provided by the image processing module 14 are categorized as needed for a particular application. For example, in the detection of deception by the subject 10, only a subset of all the spots detected and processed may be needed for deception analysis. The spots of interest are categorized in terms of their size and activity during a selected period of time, and then submitted to the next step of analysis, in which the selected and categorized spot data are compared, in block 42, with database parameters retrieved from a facial action coding system (FACS) database 44. The database 44 contains a list of all relevant combinations of speckle spot parameters, stored in association with corresponding emotions or physiological conditions. Based on this comparison with the database, the apparatus generates a report, as indicated in block 46. In addition, selected conclusions reached as a result of the analysis are transmitted to the display 16, where they are overlaid with the facial image to provide the operator with a rapid feedback of results, together with an indication of a reliability factor based on the degree to which the detected spot movements correlate with the database indications of an emotion, such as deception. In addition to this result information, the display 16 may also be overlaid with color-coded indications of muscle spot activity, which an experienced operator should be able to interpret and take appropriate action.

The various embodiments described have in common the utilization of full-frame imaging, speckle detection and tracking. The image is processed in several ways to provide useful information. The areas on the subject's face that respond to stimuli can be highlighted in the display. The frequency and duration of the response in an area can be determined and presented with an appropriate color code or other legend to aid the operator. Thresholds and filters can be implemented using conventional digital processing techniques, to maximize the sensitivity and of the instrument in detecting stress and emotional state. The patterns of excitation may also be compared to a database obtained through testing a representative population, perhaps differentiated by factors such as age, gender, ethnic origin, and so forth. By applying appropriate algorithms to the image data, physiological parameters such as pulse and cardiac waveform can be obtained along with an analysis of the patterns of facial muscle group excitations.

It will be appreciated from the foregoing that the present invention represents a significant advance in the field of facial analysis for the purpose of detecting various emotions and associated physiological conditions that manifest themselves when a subject is exposed to emotion-provoking stimuli. In particular, the invention provides for the detection and analysis of multiple facial muscle groups simultaneously, during a brief period of involuntary activity following application of an external stimulus. It will also be appreciated that, although specific embodiments of the invention have been described in detail for purposes of illustration, various modifications may be made without departing from the spirit and scope of the invention. Accordingly, the invention should not be limited except as by the appended claims.

The invention claimed is:

1. A method for sensing selected emotions in a human subject, comprising the steps of:
    implementing electronic speckle pattern interferometry to generate an image of substantially all of the face of a human subject that is a speckle-spot pattern of diffusely reflected coincident light corresponding to the face of the human subject;
    processing the image to identify movements in selected critical areas of the face based on identifying fluctuations in multiple-pixel reflectivity of the speckle-spot pattern compared with non-vibratory areas of adjacent facial surfaces;
    comparing the identified movements in the selected critical areas with a database that associates movements in selected critical areas with specific emotional and physical conditions; and
    generating a report of the emotional and physical condition of the subject.

2. A method as defined in claim 1, wherein the processing step comprises:
    inputting a two-dimensional frame of the image;
    scanning the image to locate the subject's face and determine it's relative position and extent;
    scanning the facial part of the image to detect the selected critical areas;
    repeating the preceding steps for a sequence of image frames;
    recording frame-to-frame changes in critical areas of interest; and
    recording frame-to-frame changes in critical area positions, for purposes of tracking the positions while permitting limited movement of the subject.

3. A method as defined in claim 2, wherein the step of recording frame-to-frame changes in critical areas of interest includes recording changes in at least one speckle-spot area in the critical areas of interest.

4. A method as defined in claim 2, wherein the step of recording frame-to-frame changes in critical areas of interest includes recording changes in axial distance, to facilitate detection of axial pulsing movements.

5. A method as defined in claim 1, wherein the comparing step makes use of a database that uses the facial action coding system (FACS).

6. Apparatus for sensing selected emotions in a human subject, the apparatus comprising:
    an optical imaging device configured to obtain a first image of substantially all of the face of the human subject at a beginning of a pulse period associated with a pulsed light source, to obtain a second image of substantially all of the face of the human subject at an end of the pulse period, and to subtract the second image from the first image to generate a resulting image of substantially all of the face of the human subject having a high contrast ratio;
    an image processing module, for processing the resulting image to identify movements in selected critical areas of the face;
    a database that associates groups of facial movements with specific emotional and physical conditions of the subject based on identifying fluctuations in multiple-pixel reflectivity of a speckle-spot pattern compared with non-vibratory areas of adjacent facial surfaces to identify the selected critical areas of the face;

a database analysis module, for comparing the identified movements in the selected critical areas with the database; and a report generator, for generating a report of the emotional and physical condition of the subject.

7. Apparatus as defined in claim 6, wherein the optical imaging device comprises a charged-coupled device (CCD) camera producing a two-dimensional image.

8. Apparatus as defined in claim 6, wherein the image processing module comprises:

means for inputting a two-dimensional frame of the image;

means for scanning the image to locate the subject's face and determine it's relative position and extent;

means for scanning the facial part of the image to detect the critical areas of interest;

means for repeating the preceding steps for a sequence of image frames;

means for recording frame-to-frame changes in the critical areas of interest; and means for recording frame-to-frame changes in critical area positions, for purposes of tracking the positions while permitting limited movement of the subject.

9. Apparatus as defined in claim 8, wherein the means for recording frame-to-frame changes in the critical areas includes means for recording changes in at least one speckle-spot area in the critical areas of interest.

10. Apparatus as defined in claim 8, wherein:

the optical imaging device includes means for measuring axial distance to a critical area of the face; and the means for recording frame-to-frame changes in critical area positions includes means for recording changes in axial distance, to facilitate detection of axial pulsing movements in the critical area of the face.

11. Apparatus as defined in claim 8, wherein the database uses the facial action coding system (FACS).

12. A method as defined in claim 1, wherein processing the image comprises tracking and recording frame-to-frame changes in at least one of position, size, and intensity of speckle-spots in the selected critical areas of the speckle-spot pattern.

13. A method as defined in claim 1, wherein generating the image comprises:

obtaining a first image of substantially all of the face of the human subject at a beginning of a pulse period associated with a pulsed light source;

obtaining a second image of substantially all of the face of the human subject at an end of the pulse period associated with the pulsed light source; and subtracting the second image from the first image to generate a resulting image of substantially all of the face of the human subject having a high contrast ratio.

14. Apparatus as defined in claim 6, wherein the optical imaging device implements electronic speckle pattern interferometry to generate a speckle-spot pattern of diffusely reflected coincident light that corresponds to the face of the human subject.

15. Apparatus as defined in claim 14, wherein the image processing module is configured to track and record frame-to-frame changes in at least one of position, size, and intensity of speckle-spots in the selected critical areas of the speckle-spot pattern.

* * * * *